US00PP36294P2

(12) United States Plant Patent
Bryan

(10) Patent No.: US PP36,294 P2
(45) Date of Patent: Dec. 3, 2024

(54) ***ALOCASIA* PLANT NAMED 'AMILAPGO'**

(50) Latin Name: *Alocasia macrorrhizos*
Varietal Denomination: AMILAPGO

(71) Applicant: A-Milian Nursery, Inc., Homestead, FL (US)

(72) Inventor: Kraig Bryan, Homestead, FL (US)

(73) Assignee: A-Milian Nursery, Inc., Homestead, FL (US)

( * ) Notice: Subject to any disclaimer, the term of this patent is extended or adjusted under 35 U.S.C. 154(b) by 0 days.

(21) Appl. No.: 18/831,065

(22) Filed: May 29, 2024

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

'AMILAPGO' is a new and distinctive *Alocasia* plant which is characterized by dark yellow-green foliage that is irregularly blotched and flecked with light yellow and borne on conspicuously variegated petioles, mature petioles which exhibit a plurality of greyed-purple broken and irregular transverse lines, resembling a zigzag pattern, at and near the base, and the stability of all characteristics from generation to generation.

3 Drawing Sheets

Latin name of the genus and species: The Latin name of the genus and species of the novel variety disclosed herein is *Alocasia macrorrhizos.*

Variety denomination: The inventive variety of *Alocasia* disclosed herein has been given the variety denomination 'AMILAPGO'.

BACKGROUND OF THE INVENTION

Parentage: The new plant originated as a spontaneous, partial-plant mutation. The mutation was discovered at a greenhouse in Homestead, Florida, in July of 2021, growing amongst a plurality of cultivated unnamed *Alocasia macrorrhizos* plants (not patented) which typified the species. The mutation exhibited conspicuously variegated foliage relative to the parent. The mutated plant shoot was harvested from the mother plant, repotted, and grown for an additional four months, approximately, in order to evaluate stability and uniqueness of the characteristics first observed. Upon confirmation of the stability and uniqueness, the new plant was selected for commercialization and given the name, 'AMILAPGO'.

Asexual Reproduction: Asexual reproduction of the new cultivar 'AMILAPGO', by way of vegetative division of the plant shoots, was first initiated in October of 2021 in Homestead, Florida. Eight successive generations so produced have shown that the unique features of the instant plant cultivar are stable and reproduced true to type.

SUMMARY OF THE INVENTION

The cultivar 'AMILAPGO' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Alocasia* cultivar 'AMILAPGO'. These traits, in combination, distinguish 'AMILAPGO' as a new and distinct cultivar.

1. *Alocasia* 'AMILAPGO' exhibits a large plant size with very large, cordate laminas borne on long petioles that arise directly from the base of the plant; and
2. *Alocasia* 'AMILAPGO' exhibits conspicuously variegated petioles with juvenile petioles that are light yellow with yellow-green irregular longitudinal streaking and mature petioles that are yellow-green with light yellow irregular longitudinal streaking; and
3. *Alocasia* 'AMILAPGO' exhibits greyed-purple broken and irregular transverse lines, resembling a zigzag pattern, on the lower portion of mature petioles; and
4. *Alocasia* 'AMILAPGO' exhibits dark yellow-green foliage that is irregularly blotched and flecked with light yellow; and
5. *Alocasia* 'AMILAPGO' exhibits sporadic blistering of the epidermis in the form of irregularly shaped, translucent-white blotches.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
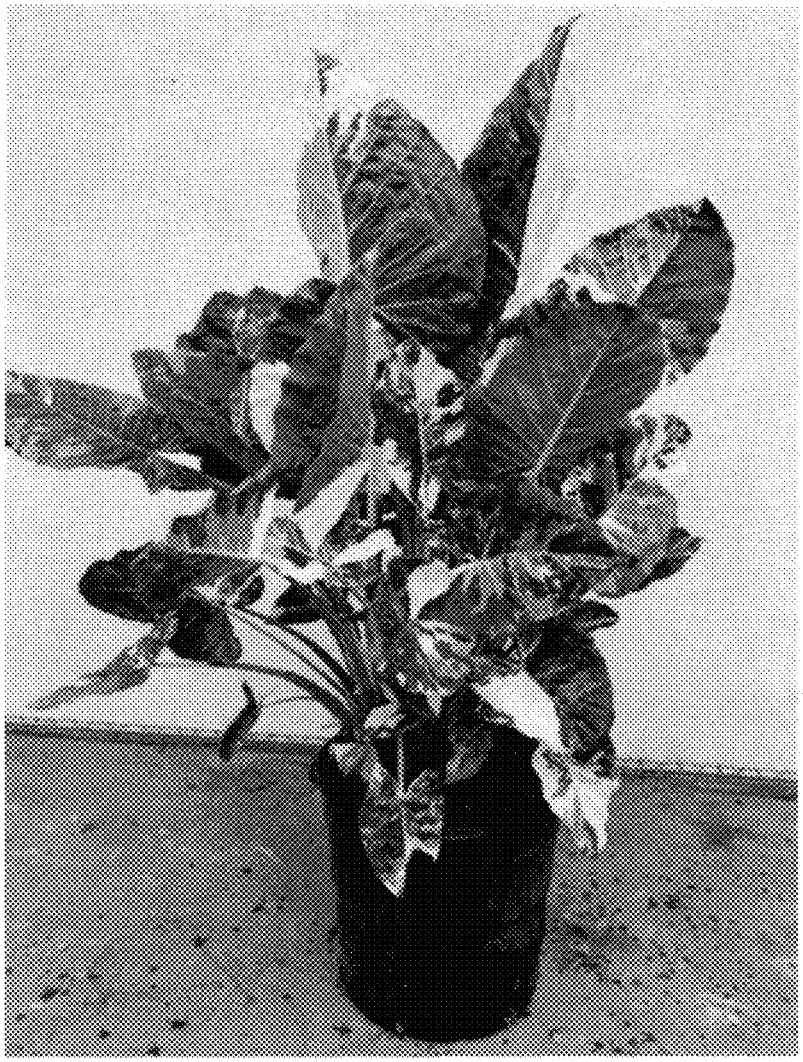
FIG. 1 shows, as nearly true as it is reasonably possible to make the same in color illustrations of this type, an exemplary plant of the new cultivar, 'AMILAPGO'. The plant shown is approximately 18 months old, grown in a 25-liter nursery container at a commercial nursery in Homestead, Florida.
Figure 2:
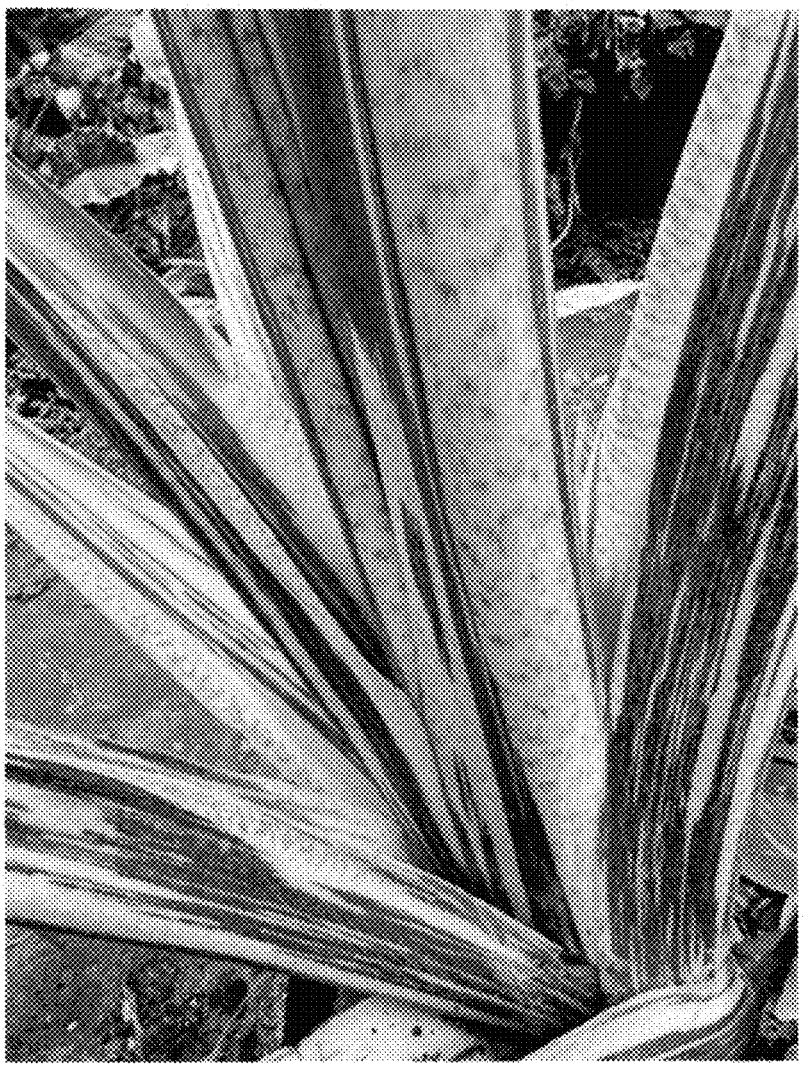
FIG. 2 shows the greyed-purple irregular transverse lines of the mature petioles of 'AMILAPGO'.
Figure 3:
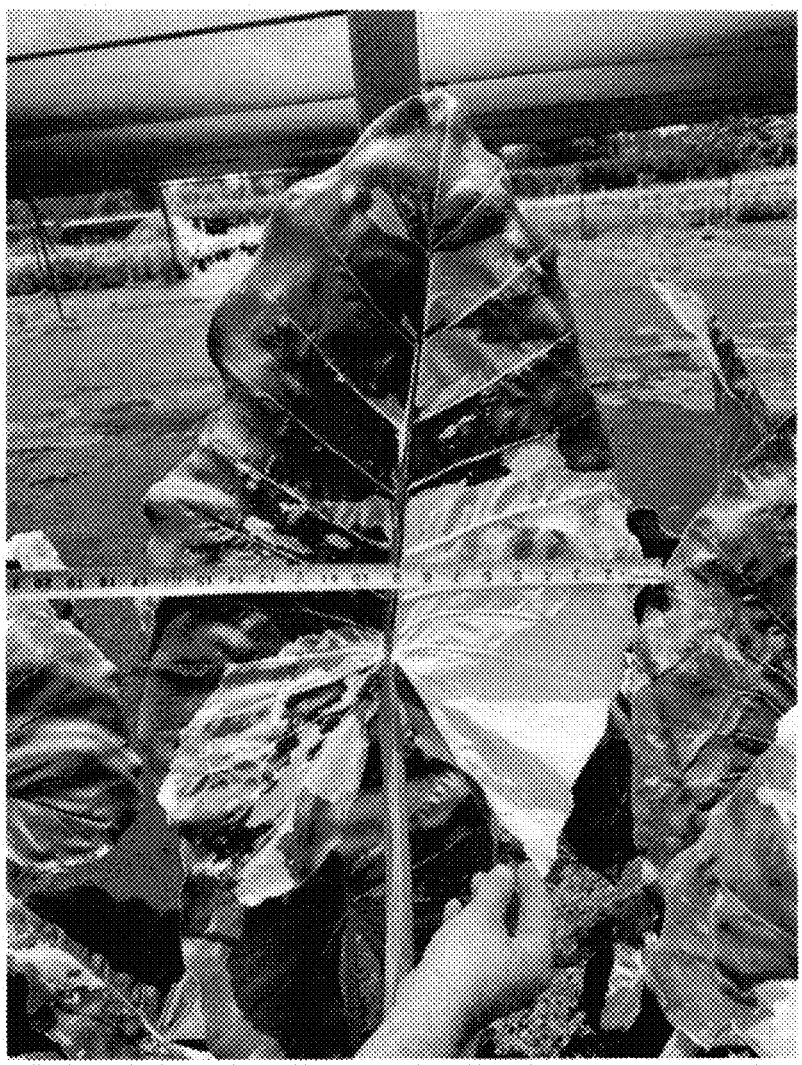
FIG. 3 shows the adaxial surface of the mature foliage of 'AMILAPGO'.

The following observations and measurements made in October of 2023 describe an 18-month-old 'AMILAPGO' plant grown in a 25-liter nursery container at a commercial nursery in Homestead, Florida. Said plant was produced under 63 percent shade, using conventional production protocols for *Alocasia* species. Cultural practices consisted of overhead irrigation once the top 5 cm of potting media becomes dry, seasonal applications of a 18-8-12 slow-release granular fertilizer, and preventative applications of insecticide and fungicide.

Those skilled in the art will appreciate that certain characteristics will vary with older or, conversely, with younger plants. 'AMILAPGO' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on *The Royal Horticultural Society Colour Chart*, The Royal Horticultural Society, London, third edition.

A botanical description of 'AMILAPGO' and comparisons with the parent plant and the most similar variety of common knowledge are provided below.

General plant description:

*Growth habit*.—Clumping herbaceous perennial; acaulescent, with foliage arising directly from the base of each clump.

*Plant growth habit profile*.—Vase-shaped.

*Height*.—183 cm.

*Width*.—Average 152 cm.

*Growth rate*.—Moderately fast-growing.

*Plant vigor*.—Moderately to highly vigorous.

*Propagation*.—Method — Vegetative division of the plant shoots. Time to initiate roots — Approximately 4 to 6 weeks to initiate roots at an average ambient temperature of 21 degrees Celsius. Crop time — Approximately 16 to 20 weeks to produce a well-rooted, marketable 17 cm container from a rooted cutting.

*Environmental tolerances*.—Moderately high tolerance to rain; moderate tolerance to wind; not drought tolerant; tolerant of temperatures to at least 40 degrees Celsius. Cold hardy to USDA Hardiness Zone 8.

*Pest resistance and susceptibility*.—Plants have not been observed to be any more or less susceptible or resistant to pathogens and pests common to *Alocasia* sp.

Root system:

*General*.—*Alocasia* sp. exhibits a shallow root system with fleshy adventitious roots arising from large corms.

*Branching*.—Freely branched.

*Density*.—Moderately dense.

*Distribution*.—Relatively shallow.

*Texture*.—Fleshy; smooth; lacking root hairs.

Stems:

*Branching characteristics*.—*Alocasia* sp. is acaulescent; not stems or lateral branches are produced.

Foliage:

*Arrangement*.—Basal foliage is alternate to spiraled.

*Division*.—Simple.

*Attachment*.—Petiolate.

*Quantity of leaves per shoot*.—Approximately 12 to 14.

*Lamina*.—Shape — Hastate. Apex — Acuminate. Base — Cordate; lobes free. Aspect — Near flat to concave. Attitude — Leaves emerge in the same plane as the petiole yet mature to oblique or pendulous. Dimensions — 43.0 cm long and 68.0 cm wide at maturity. Margin — Entire; strongly undulated. Texture and luster, adaxial surface — Rugose, glabrous, and slightly to moderately glossy. Sporadic blistering of the epidermis is present in the form of irregularly shaped, translucent-white blotches. Texture and luster, abaxial surface — Rugose, glabrous, slightly glossy. Juvenile color, adaxial surface — Yellow-green, nearest to RHS 147A; irregularly flecked and blotched with light yellow, nearest to RHS 8D. Additionally, the areas of the laminar surface with epidermal blistering appear as translucent-white blotches, RHS 155A, revealing the light-yellow flecks and blotches beneath. Where epidermal blistering occurs on the yellow-green portions of the lamina, the color generally appears to be greyed-green, nearest to 194B. Juvenile color, abaxial surface — Yellow-green, nearest to RHS 144A yet darker; irregularly flecked and blotched with light yellow, nearest to RHS 8D. Additionally, the areas of the laminar surface with epidermal blistering appear as translucent-white blotches, RHS 155A, revealing the light-yellow flecks and blotches beneath. Where epidermal blistering occurs on the yellow-green portions of the lamina, the color generally appears to be greyed-green, nearest to 194B. Mature color, adaxial surface — Yellow-green, nearest to RHS 147A; irregularly flecked and blotched with light yellow, nearest to RHS 8D. Additionally, the areas of the laminar surface with epidermal blistering appear as translucent-white blotches, RHS 155A, revealing the light-yellow flecks and blotches beneath. Where epidermal blistering occurs on the yellow-green portions of the lamina, the color generally appears to be greyed-green, nearest to 194B. Mature color, abaxial surface — Yellow-green, nearest to RHS 144A yet darker; irregularly flecked and blotched with light yellow, nearest to RHS 8D. Additionally, the areas of the laminar surface with epidermal blistering appear as translucent-white blotches, RHS 155A, revealing the light-yellow flecks and blotches beneath. Where epidermal blistering occurs on the yellow-green portions of the lamina, the color generally appears to be greyed-green, nearest to 194B. Venation — Vein pattern — Pinnate. Vein color, adaxial surface — The coloration of the veins varies from solid yellow-green (RHS 147A) to yellow-green and blotched, flecked, or streaked with yellow (RHS 147A and 8D, respectively); occasionally some lateral veins will be solid yellow, RHS 8D. Vein color, abaxial surface — In general, the main vein and lateral veins are yellow-green, RHS 144B. However, in the flecked or blotched portions of the lamina, the veins may also be colored yellow, nearest to RHS 8D.

*Petiole*.—Attachment — Sheathed. Aspect — Subterete at the proximal end; terete at the union with the lamina. Length — Ranging from 65 to 80 cm. Width — 5.5 cm at the base. Strength — Moderately strong. Texture — Smooth and glabrous. Luster — Very slightly glossy. Color, juvenile petioles — Light yellow, nearest to in between 8D and 10D, with yellow-green irregular longitudinal streaking, RHS 144A. Color, mature petioles — Yellow-green, RHS 144A, with light yellow irregular longitudinal streaking, nearest to a mixture of RHS 8D and 10D. The lower portion of the petioles exhibit an abundance of greyed-purple broken and irregular transverse lines, resembling a zigzag pattern, nearest to in between RHS 184B and 185B.

Inflorescence: *Alocasia* typically produces a spathe and spadix inflorescence, but no flowering of the claimed plant has been observed to date.

Flower buds: No flowering has been observed to date.

Flowers: No flowering has been observed to date.

Reproductive organs: No flowering has been observed to date.

Seed and fruit: Seed production has not been observed.

COMPARISONS WITH THE PARENT

Plants of the new cultivar 'AMILAPGO' may be distinguished from the parent, an unnamed *Alocasia macrorrhizos* plant (not patented), by the characteristics described in Table 1.

TABLE 1

| Characteristic | 'AMILAPGO' | The parent. |
|---|---|---|
| Presence of foliar variegation. | Present. | No variegation is present. |
| General coloration of the Petiole. | Yellow-green with light yellow irregular longitudinal streaking; lower portion of the petioles exhibit an abundance of greyed-purple broken and irregular transverse lines, resembling a zigzag pattern. | Solid yellow-green to green with no greyed-purple transverse, zigzag lines are present. |

TABLE 1-continued

COMPARISONS WITH THE MOST SIMILAR COMMERCIAL VARIETY

Plants of the new cultivar 'AMILAPGO' may be distinguished from the most similar commercial comparator known to the inventor, *Alocasia odora* 'Variegata' (not patented), by the characteristics described in Table 2.

TABLE 2

| Characteristic | 'AMILAPGO' | 'Variegata' |
|---|---|---|
| General coloration of the petiole. | Yellow-green with light yellow irregular longitudinal streaking; lower portion of the petioles exhibit an abundance of greyed-purple broken and irregular transverse lines, resembling a zigzag pattern. | Yellow-green with irregular longitudinal white striping; no greyed-purple transverse, zigzag lines are present. |
| Foliar sinus. | More closed. | More open. |
| General coloration of the mature foliage. | Dark yellow-green and flecked and blotched with light yellow. | Dark yellow-green and fleck and blotched with a darker shade of yellow relative to 'AMILAPGO'. |
| Hardiness. | Less hardy than the 'Variegata'. | Hardier than 'AMILAPGO'. |

That which is claimed is:

1. A new and distinct variety of *Alocasia* plant named 'AMILAPGO', substantially as described and illustrated herein.

* * * * *